United States Patent [19]
Dance et al.

[11] Patent Number: 5,634,897
[45] Date of Patent: Jun. 3, 1997

[54] RHEOLYTIC OCCLUSION REMOVAL CATHETER SYSTEM AND METHOD

[75] Inventors: Creg W. Dance, Elk River; Steven J. Erb, Eden Prairie, both of Minn.

[73] Assignee: Lake Region Manufacturing, Inc., Chaska, Minn.

[21] Appl. No.: 134,089

[22] Filed: Oct. 8, 1993

[51] Int. Cl.$^6$ .................................................. A61M 1/00
[52] U.S. Cl. .............................. 604/35; 604/28; 604/96; 606/180
[58] Field of Search ................................ 604/96, 22, 28, 604/19, 35, 95, 98, 131, 264, 27, 43, 52, 54; 606/167, 170, 180

[56] References Cited

U.S. PATENT DOCUMENTS

| | | |
|---|---|---|
| 4,445,509 | 5/1984 | Auth . |
| 4,589,412 | 5/1986 | Kensey . |
| 4,631,052 | 12/1986 | Kensey . |
| 4,747,821 | 5/1988 | Kensey et al. . |
| 4,749,376 | 6/1988 | Kensey et al. . |
| 4,784,636 | 11/1988 | Rydell . |
| 4,790,813 | 12/1988 | Kensey . |
| 4,795,438 | 1/1989 | Kensey et al. . |
| 4,857,045 | 8/1989 | Rydell . |
| 4,950,238 | 8/1990 | Sullivan . |
| 5,135,482 | 8/1992 | Neracher . |
| 5,135,484 | 8/1992 | Wright . |
| 5,273,526 | 12/1993 | Dance et al. . |

OTHER PUBLICATIONS

"Rheolytic Catheter for Percutaneous Removal of Thrombus," Radiology, vol. 182, No. 1, Jan. 1992, pp. 263–267.
"A Rheolytic System for Percutaneous Coronary and Peripheal Plaque Removal," Angiology, vol. 42, No. 2, Feb. '91, p. 90.

*Primary Examiner*—V. Millin
*Assistant Examiner*—N. Kent Gring
*Attorney, Agent, or Firm*—Grady J. Frenchick; Stroud, Stroud, Willink, Thompson & Howard

[57] ABSTRACT

A catheter for insertion in body vessels for removing occlusions or obstructions such as thrombus, clot, plaque and other vascular or arterial deposits without generating distal emboli. Removal of freshly or recently formed obstructions is a preferred application. Concurrently or subsequently, suction or aspiration removal of the resulting occlusion debris is disclosed. A catheter system of this invention comprises elongate, hollow, inner and outer coaxial catheters having distal and proximal ends. The distal end of the outer catheter terminates short of the distal end of the inner catheter. The catheters may be independently movable with respect to each other. The inner catheter wall defines a central lumen which fluidically couples the proximal and distal ends of the inner catheter and through which a guidewire can pass. The central lumen has a reduced diameter distal portion which, with an occluder means (e.g., a guidewire), is adapted to restrict distal fluid delivery therethrough. The distal end of the inner catheter is fluidically coupled to a diffusion manifold which includes a plurality of fluid diffusion orifices. Located between the diffusion manifold and the distal end of the outer catheter is a diffuser. The diffuser, which may be fixedly or rotatively mounted, is located so that fluid exiting from the diffusion orifices impinges thereon and is dispersed toward the occlusion.

22 Claims, 11 Drawing Sheets

RHEOLYTIC OCCLUSION REMOVAL CATHETER SYSTEM AND METHOD

BACKGROUND OF THE INVENTION

1. Field of the Invention

This invention relates to vascular occlusion removal or thrombus dissolution or destruction devices. More specifically, this invention relates to fluid driven thrombus dissolution catheter systems or catheters. Yet more specifically, this invention relates to apparatuses or thrombectomy catheters for removing vascular obstructions by the creation of a dissolution turbulence or vortex near or adjacent to such obstruction. Catheters of this invention are designed for insertion in body vessels for removing occlusions or obstructions such as thrombus, clot, plaque, emboli, and other vascular or arterial deposits. A particularly important application of the present invention is the dissolution and removal of freshly or recently deposited thrombi and other newly-formed varieties of obstruction referred to above. Concurrently or subsequently, suction or aspiration removal of the resulting occlusion disintegration products is described. Removal of such products provides the decided advantage of reducing possible adverse impact upon downstream or distal organs of occlusion debris. The likelihood of occurrence of macroembolization, distal embolization, and distal infarction are thereby significantly reduced.

2. Description of the Prior Art

The removal of harmful blockages from vessels, ducts, arteries or other passages within the body (sometimes collectively referred to here as "vessels") is typically accomplished by one of several techniques. One technique, balloon angioplasty, involves deployment of a balloon catheter within the obstructed vessel so that, when the balloon is inflated, the constriction or obstruction material is compressed against the vessel walls.

U.S. Pat. No. 4,950,238 issued to Dennis E. Sullivan describes a hydro-rotary vascular catheter which is a variation on the balloon angioplasty. Sullivan discloses a catheter having a rotatable, fluid-directing head. The head of the Sullivan device directs fluid distally, i.e., downstream from the catheter. The Sullivan device further includes an isolation means, e.g., balloons, which are positioned upstream and downstream of the obstruction. After being positioned, the upstream and downstream balloons are inflated with the patient's blood and a pressurized flushing fluid, respectively, to seal off the obstruction. Flushing fluid is ejected distally from the rotary fluid-directing head of the Sullivan catheter which causes the head to rotate. This rotation creates turbulence which, in conjunction with the fluid streams themselves, is disclosed to break down the vessel obstruction. A return channel permits debris to be removed from the constricted area.

The Sullivan device is structurally complicated and has the admitted drawback of occasionally requiring the use of digestive enzymes or other solvents such as those used in some forms of vascular treatment discussed above. Sullivan also requires a shield over the radially oriented fluid-directing orifice to prevent vessel damage due to direct impingement of fluid exiting from the catheter. Further, the Sullivan device is not capable of being precisely placed within the vasculature because it has no structure which would permit it to track a, e.g., steerable guidewire. A problem with both of the above techniques is that they may cause blood vessel wall damage by stretching of the tunica intima and tunica media layers.

A more recent technique, laser angioplasty, uses laser energy to vaporize an obstruction. A typical example of a laser angioplasty catheter is described in U.S. Pat. No. 4,685,458 to Leckrone. As is disclosed in the Leckrone '458 patent, the catheter, which is mounted for rotation and translation about a filament, has a pair of abutments disposed on its distal end. Also included on the distal end of the catheter is a bladder which, when inflated, causes the abutments to bear against the inner surface of the blood vessel so that the space between the abutments defines a working chamber for delimiting the area around an obstruction. A fiber optic connected to a source of laser energy which extends through the catheter, with the distal end of the fiber optic being disposed in one of the abutments. In addition, a suction port is provided between the abutments for removing disintegrated material from the delimited area. Severing means such as a blade or a heated element also may be included for severing and releasing material which is not vaporized by the laser. As with balloon angioplasty, laser angioplasty can result in damage to the blood vessel itself.

Another technique for removal of blockages utilizes what is generally referred to as an atherectomy device or atherectomy catheter. An example of this type of device is disclosed in U.S. Pat. No. 4,631,052 to Kensey. The device of the Kensey '052 patent comprises a bladed cutting head which is rotated by a turbine drive to cut away occlusions in a body vessel. The catheter disclosed in the Kensey '052 patent permits the possibility of vessel wall damage if its rotary head were to be deflected by an especially hard portion of an occlusion.

U.S. Pat. No. 4,747,821 to Kenneth Kensey, et al. discloses a catheter with a high speed moving working head. At several places in the '821 patent the potentially harmful impact of particles generated from a vascular occlusion upon down stream organ structures is recognized. The Kensey, et al. '821 patent deals with the problem by providing a mechanically driven catheter utilizing a pair of non-sharp, impacting surfaces. The impacting surfaces allegedly emulsify the obstruction by repeatedly recycling the dissolution products against the non-sharp impacting surface by means of a distally-emitting vortex flow. No aspiration or removal of dissolution products is disclosed or suggested because removal of the emulsified dissolution products is disclosed to be unnecessary.

U.S. Pat. No. 4,749,376 to Kenneth Kensey et al. discloses a "Reciprocating, Working Head Catheter". The catheter of the Kensey et al. '376 patent comprises an elongated drive wire extending through the catheter body and a motion translator located at the distal end of the catheter. The drive wire is rotated at high speed and the translator translates the rotary motion into reciprocating motion. In this manner the working head is rotated and reciprocated. This motion, in conjunction with a fluid, permits the catheter to open the body vessel in which it is inserted. No aspiration or removal of debris is disclosed or suggested in the Kensey et al '376 patent.

U.S. Pat. No. 4,445,509 to David C. Auth discloses a rotating head cutting tool recanalization catheter having spirally shaped cutting flutes with hardness-differential cutting properties. Plaque and other obstructions are alleged to be removed from organic structures without damage to normal tissue. The cutting apparatus of the Auth et al. patent is disclosed to be rapidly rotated within the blood vessel of a patient by means of an external torque-generating device, e.g., an electric motor. In operation, then, the cutting tool is advanced against a blood vessel lesion or obstruction and the obstruction is differentially cut. The apparatus of Auth et al. has a fluid port in communication with an external suction device so that blood and debris from the cutting operation can be removed from the cutting site.

U.S. Pat. No. 4,631,052 to Kenneth R. Kensey discloses a rotating head or recanalization catheter which is advanced through the body passageways to the site of a restriction. The apparatus of the Kensey '052 patent is disclosed to operate by cutting or by mechanically beating or otherwise agitating or disturbing the blockage material to form an opening. A perfusion structure is provided which provides oxygenated fluids, drugs, contrast media or dyes into the occluded or blocked passage way. U.S. Pat. No. 4,795,438 also to Kenneth Kensey discloses a method and apparatus for forming a restriction in a vessel, such as a fallopian tube. No removal of unwanted vascular obstructions is disclosed or contemplated in the Kensey '438 patent.

U.S. Pat. No. 4,784,636 to Mark A. Rydell discloses a balloon atherectomy catheter. The Rydell '636 patent apparatus has an angular cutting tip fixed to the distal end of an elongated drive tube. A separate rotational drive mechanism is coupled to the drive tube to rotate the drive tip. Provision is made for introducing fluid through the loop of the guide catheter for inflating the balloon and for aspirating blood and loose particles away from the occlusion site. The balloon mechanism is used primarily to retain the distal end of the catheter assembly in place near the occlusion to permit the cutting operation to be performed.

U.S. Pat. No. 5,135,484 to John T. M. Wright discloses a method of removing plaque from vessels in which a partially isolated portion of a vessel (containing an occlusion) is exposed to a slurry. The slurry abrades the plaque and is subsequently withdrawn from the isolated vessel segment.

U.S. Pat. No. 4,715,538 to Horst Lingnau and U.S. Pat. No. 3,120,326 to Ernie D. Willhoite disclose jet nozzles and rotary spray devices, respectively. The inventions of Lingnau and Willhoite are useful for cleaning narrow tubular parts, such as pipes, or for drilling though soft materials by means of Jet or spray nozzles. These references make no mention of possible medical applications of these inventions.

Commonly assigned, published Patent Cooperation Treaty Application PCT/US05220 describes a hydro-rotary thrombectomy catheter which employs a catheter head which is affirmatively rotated, e.g., by means of a cable. The catheter of the '05220 application, therefor, has separate structures to rotate the catheter head, deliver fluid and retrieve fluid and debris from the occlusion site.

Applicants are aware of descriptions of a catheter which comprises a distal end header in fluid communication with a plurality of proximal end- or backward-directed high pressure Jets. The method of operation of such a device is described in an Abstract appearing at Volume 42 of ANGIOGRAPHY, "A Rheolytic System for Percutaneous Coronary and Peripheral Plaque Removal" p. 90 February, 1991. No description of the device is contained in that Abstract. A description of what is thought to be that device appears at 182 RADIOLOGY January, 1992 pp. 263–267 and in the NEW YORK TIMES, Sunday Mar. 21, 1993, section 3. That device is apparently being developed by Possis Medical, and has been offered under the trade designation "AngioJet". Fluids such as saline under high pressure are fed to the distal end of the catheter through the catheter body by means of an off-center input pipe or lumen. The high pressure fluids then are used to break up the occlusion. No rotation of any part of the device is suggested.

None of the above disclosures alone or in combination disclose or suggest the invention of the present application. This invention overcomes the disadvantageous of prior art devices by providing a catheter which can generate a uniquely placeable and controllable, atraumatic, zone of dissolution. The present catheter is reliable, having a relatively uncomplicated structure. The catheter by itself or in conjunction with other devices is widely applicable to the removal of obstructions in both peripheral and coronary applications.

BRIEF SUMMARY OF THE INVENTION

The present invention, in one aspect, is a catheter for removing an obstruction in a body vessel which generally involves no cutting or mechanical destruction of the obstruction or deposit. In a preferred practice of this invention, no physical contact is necessary between any part of the catheter and the obstruction. After placement e.g., by means of a steerable guidewire, a device of this invention effectuates removal of the obstruction or deposit by the creation of a controlled, atraumatic, preferably distally-directed, fluid vortex, zone of turbulence, or dissolution zone in the region immediately adjacent the obstruction. This controlled vortex effectuates destruction and removal of the occlusion without traumatizing any part of the adjacent vessel structure. In optional practices of this invention, balloons alone or in combination with radiopaque markers are utilized to monitor and control the dissolution procedure.

In an alternative embodiment, a proximal balloon is used to isolate the portion of the vasculature which is to be treated. By utilization of this invention, the obstruction is removed from the vessel without injury or damage to the surrounding vessel walls. This is accomplished, in part, by the elimination of need for actual physical contact between the obstruction and any part of the catheter. Occlusion debris is aspirated from the site of the occlusion to the outside, proximal end of the catheter, thereby reducing the likelihood that distal embolization problems will arise. Lastly, this invention is particularly well suited to destruction and removal of recently-formed or fresh thrombus, i.e., thrombus formed within about the previous 5 hours to 30 days.

A catheter assembly or system of the present invention comprises elongate, hollow, inner and outer concentric or coaxial catheters or catheter bodies, each of the bodies having distal and proximal ends. The distal end of the outer catheter terminates short of the distal end of the inner catheter so that a portion of the inner catheter projects therefrom. As is described in greater detail below, the catheter bodies may be independently movable with respect to each other or they may be fixed with respect to each other. The catheter bodies each have inner and outer walls. The inner catheter wall defines a central lumen which fluidically couples the proximal and distal ends of the inner catheter and which has an interior diameter large enough to permit a guidewire to pass therethrough. The central lumen defined by the inner catheter body has a reduced or lesser diameter or distal portion which is adapted to cooperate with a separate occluder means (e.g., a guidewire) so as to restrict distal fluid delivery through said central lumen. The distal end of the inner catheter is fluidically coupled to a diffusion manifold. The diffusion manifold includes a plurality of fluid orifices or ports which, in a preferred practice, deliver fluid generally proximally.

Located between the distal end of the outer catheter and the diffusion manifold orifices is a diffuser. The diffuser can be mounted on or molded into the diffusion manifold or the inner catheter wall. The diffuser may be fixedly or rotatively mounted on its supporting structure. The diffuser is located so that fluid exiting from the diffusion orifices impinges thereon and is substantially radially deflected or dispersed toward the vascular occlusion. Thus the advantageous, atraumatic vortex or zone of thrombus dissolution of this invention is generated. The radially deflected fluid is directed toward the occlusion with controlled pressure and direction so as to create an vortex or zone of dissolution which destructs the occlusion without damaging adjacent tissue. By this procedure, thrombus is pulverized or emulsified.

Between the inner and outer catheters, and defined by their outer and inner walls respectively, is an annular lumen. The annular lumen is fluidically proximally coupled to an aspiration means. In one embodiment of this invention the aspiration means comprises a luer coupler and a vacuum source connected to through the outer catheter wall. The annular lumen is employed to aspirate occlusion debris to the proximal end and ultimately out of the device for removal.

In an optional practice of the above invention, the proximal ends of the inner and outer catheters are connected to means which permit independent adjustment of the coaxial relationship between the catheter bodies (i.e., the extent of their overlap). For example, a handle and slide mechanism can be used to change or adjust the coaxial relationship between the inner catheter and outer catheters. In such an arrangement one of the other of the catheters would be substantially fixed on the handle mechanism while the slider mechanism would be fixed to the other catheter. Thus, operation of the slide would lengthen or shorten the distance between the orifices and the distal end of the outer catheter. Adjustment of the diffusion zone linear dimension can be made separately or simultaneously with generation of the atraumatic fluid zone of dissolution as described above. Adjustment of this relationship permits the user to control the separation distance between fluid output from the diffuser manifold and fluid input or aspiration into the annular lumen. Control of this separation distance (and whether or not a rotatable diffuser means is used) permits control of dissolution zone dimension and destructive force. In conjunction with control of fluid pressure, diffuser external configuration (and its rotatability), the longitudinal size, direction, radial dimension, impinging pressure and therefor the aggressiveness of the zone of dissolution can be precisely controlled.

In an optional practice of this invention, the outer catheter includes on its exterior an inflatable proximal balloon, the balloon being coupled to balloon inflation means. One or more radiopaque marker bands also may be located on the outer catheter. The number and location of radiopaque marker bands to indicate catheter structure and location is within the skill of one familiar with that art.

In a method according to the present invention, a catheter system or assembly comprising inner and outer catheter bodies, and defining an inner lumen as set forth above, is advanced over a guidewire to where its distal, working portion is located proximate the site of a previously identified vascular occlusion. The reduced interior diameter portion of the inner catheter distal tip guidewire lumen in conjunction with the guidewire itself substantially prevents fluid from being delivered distally from the catheter. A fluid zone of turbulence is created by introducing fluid into the proximal portion of the catheter, the fluid travelling through the catheter's interior lumen and emerging from the orifices in the diffusion manifold. The emerging fluid is directed from the manifold to impinge upon the diffuser, and ultimately toward the obstruction. In optional practices of this invention, saline solution containing radiopaque dye may be used in the dissolution process to permit the process and the dissolution zone to be monitored by fluoroscope. Further, the diffuser itself may comprise a radiopaque or partially radiopaque material to make identification of its location more easily accomplished. Diffuser materials would include metals, polymers, and polymer/metal compositite materials. The prarticular material selected will be determined by the intended usage, i.e., the extent of fluoroscopic examination. Concurrently, aspiration is initiated through the outer catheter to remove emerging fluid and suspended occlusion debris.

In one embodiment, the diffuser also is rotated by the fluid emerging from the orifices and impinging thereon. In a further embodiment the transverse length dimension of the zone of dissolution (or turbulence) is adjusted by changing the length of inner catheter which projects beyond the proximal end of the outer catheter. This adjustment changes the separation distance between the point where fluid emerges from the diffusion manifold on the inner catheter and the point where fluid and debris are aspirated into the outer catheter.

In preferred practice of the present method, the zone of dissolution is substantially conical with the subtended cone defining an angular relationship with respect to the axis of the device wherein the interior angle of the cone falls in the range of about 5 to about 75, preferably about 20 to about 45. In another preferred practice of this invention, recently deposited thrombus is removed from the vascular structure.

The catheter then is connected to external debris removal means, e.g., an aspirator, and external fluid input means, e.g., a pump. Pressurized fluid then is input to the vessel adjacent to site of the obstruction and the diffuser. The pressurized fluid exits the diffusion manifold and impinges upon the diffuser to create a vortex or zone of turbulence which tends efficiently to emulsify and remove the adjacent obstruction without damaging vessel structures. The external debris removal means (e.g., suction) proximally coupled to the annular lumen may be simultaneously or subsequently activated so as to remove particles generated from the obstruction by the turbulence. In this manner, removal of the vessel obstruction, and especially generated debris generated therefrom, is accomplished. It will, of course, be necessary for the rates of output and input of the fluid input means and the debris recovery means to be adjusted so that the vessel diameter is not significantly compromised.

Throughout the description of the present invention, the terms "vessel" or "vessel body" are intended to be broadly construed to include essentially any vessel, including veins and arteries, whether they are of a coronary or peripheral nature. Moreover, while the disclosure here is specifically in terms of human body vessels, removal of obstructions from essentially any body vessel is contemplated by this invention.

BRIEF DESCRIPTION OF THE DRAWINGS

The above invention will now be illustrated by reference to the detailed description below and the attached Figures wherein like reference numerals are used to refer to like features in the various views and wherein.

DETAILED DESCRIPTION OF THE INVENTION

The fluid-driven or rheologic catheter system of this invention is designed to function as an intravascular unit for the effective dissolution and extraction of thrombus in the vasculature. Its structure permits controlled, pressurized fluid infusion at the distal tip of the catheter through, in a preferred practice, a helically slotted rotor or diffuser. Passage of the pressurized fluid through the rotor, in this preferred practice, induces rotational action of the rotor that disperses the fluid, in a uniform, generally proximally directed, controllable conical pattern. The dispersed fluid substantially atraumatically impacts surrounding vascular structure. However, when thrombus is exposed to the pressurized fluid spray generated by this catheter, a dissolution, emulsification or liquification process occurs with the resulting effluent (which contains suspended occlusion debris) being aspirated away from the occlusion site through a separate catheter lumen. Aspiration of thrombus dissolution products from the thrombus site tends to reduce particulate embolization and to enhance vessel patency.

A catheter assembly of this invention tracks a guidewire (e.g., a 0.014 inch diameter guidewire) to facilitate vessel positioning for thrombus dissolution and extraction. A guidewire useable with this catheter is preferably silicone coated for improved vascular tracking and catheter interface at the close tolerance fit between the guidewire and the central lumen. Other coatings may be applied depending upon user preference.

A catheter system of this invention is intended for both coronary and peripheral vascular applications. The preferred clinical application is for the rheolytic dissolution and extraction of soft thrombus from the vasculature. This invention, therefore, is to be understood to be particularly adapted to remove relatively soft, semi-fibrotic, non-calcified thrombus. The pressurized fluid dissolution zone naturally adjusts to the vessel lumen size with no adverse effects upon the vessel wall layers. Effluent is removed from the vasculature to eliminate particulate embolization, to provide for improved vessel patency for immediate restoration of blood flow, and to expose other disease conditions that may require adjunctive interventional therapy.

Figure 1:
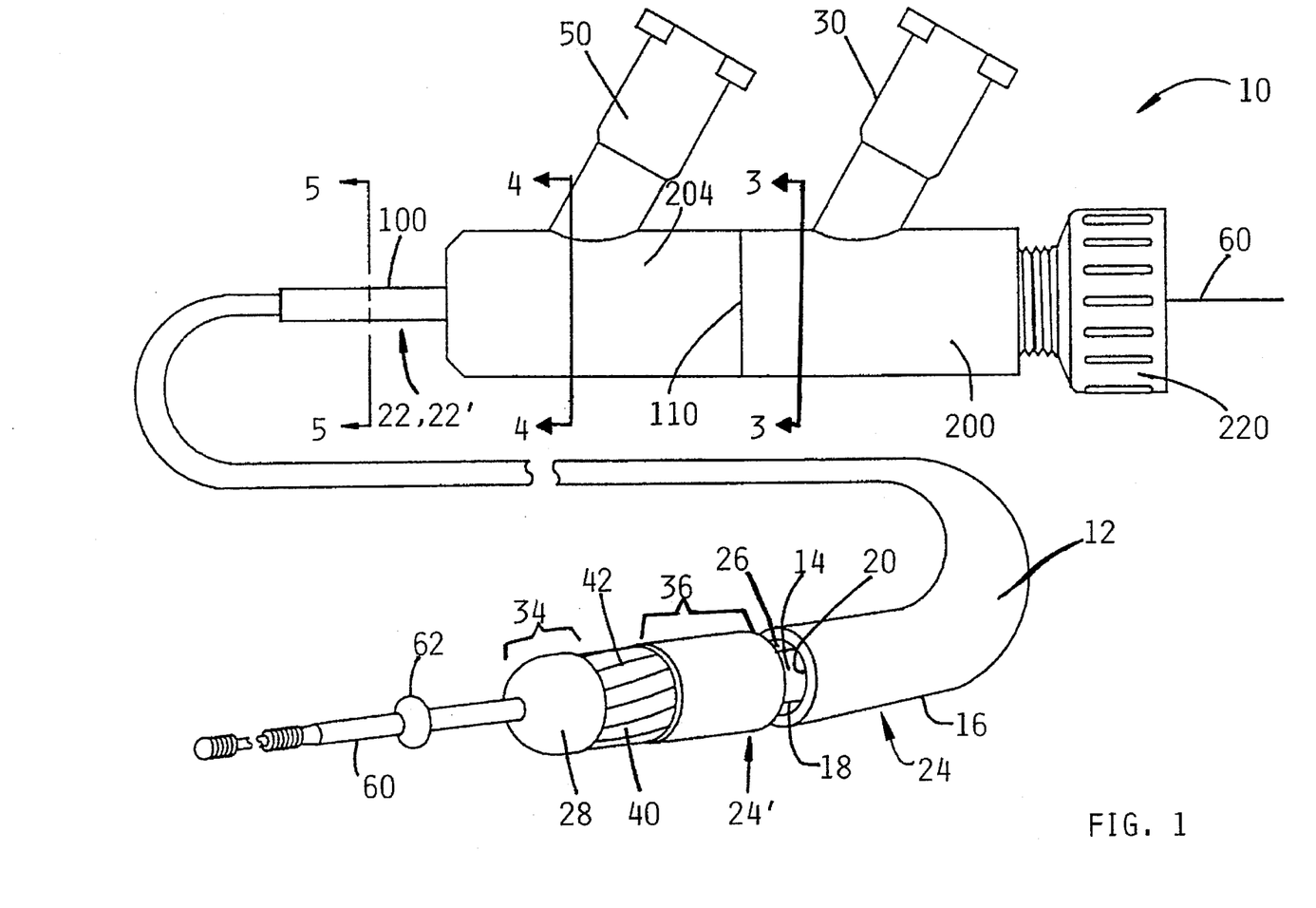
FIG. 1 is a schematic plan view of an embodiment of the present invention.

With specific reference to FIG. 1, there is shown in perspective, a catheter or catheter system 10 of the present invention. A middle segment of the multiple lumen catheter body has been deleted to permit the entire catheter to be depicted. Catheter 10 comprises outer and inner catheter bodies 12, 14, which are substantially coaxial. Catheter bodies 12 and 14 have outer walls or sides 16, 18, respectively, with outer catheter body 12 also having an indicated inner catheter wall 20. (Inner catheter body 14 also has an inner catheter wall which cannot be seen in FIG. 1.) Catheter bodies 12 and 14 both have proximal ends 22, 22' and distal ends 24, 24' which overlap in at least some portion. As is shown, the distal portion or segment 24' of the inner catheter body wall extends beyond the distal portion 24 of the outer catheter body wall. By this arrangement, catheter body walls 12, 14 cooperate to define an annular lumen 26, (more completely discussed below) which permits fluid and dissolution products to be extracted from the site of occlusion removal.

Located on the distal end 24' of inner catheter body wall 14 and in fluid communication with the interior thereof is a diffusion manifold 28. Diffusion manifold 28 is fluidically coupled (via a central lumen not shown in FIG. 1) to the proximal end of catheter system 10 (e.g., at luer coupler 30) and to a plurality of substantially radially directed orifices (not shown in FIG. 1). Diffusion manifold 28 comprises, in this embodiment, distal and proximal larger diameter segments 34, and 36, respectively, with a smaller diameter medial segment 38 therebetween. Larger diameter segments 34, 36 have a diffuser means 40 located therebetween. In the embodiment depicted in FIG. 1, diffuser means 40 is a cylindrical ring structure having a helical groove 42 embossed or cut in its exterior. Also in the embodiment shown, diffuser means 40 is rotated by fluid emerging from diffusion manifold 28. Thus, diffusion manifold 28, in this embodiment, comprises much of the structure which permits fluid to be delivered to a situs near or adjacent an occlusion.

Located on the proximal end of catheter 10 is a second luer connector 50 which is fluidically coupled (via the annular lumen) to an exterior aspiration source. In this manner, i.e., via luer couplers and lumens, fluid is both delivered to the distal end of the catheter system, is proximally directed and radially redirected, and fluid and debris are aspirated from the proximal end of the catheter. The rotatively directed fluid emerging from the diffusion manifold effects occlusion destruction with little or no vessel wall damage.

Lastly, as shown, catheter system 10 tracks a guidewire 60. Guidewire 60 passes axially through catheter 10 via the central lumen defined by inner catheter body inner wall 18. Guidewire 60 is approximately coincident with the axis of the catheter system 10. Guidewire 60 has an enlargement 62 thereon which prevents the guidewire from being completely drawn into the catheter system and which provides for retention of any structures aligned on the guidewire should they become detached.

Figure 2:
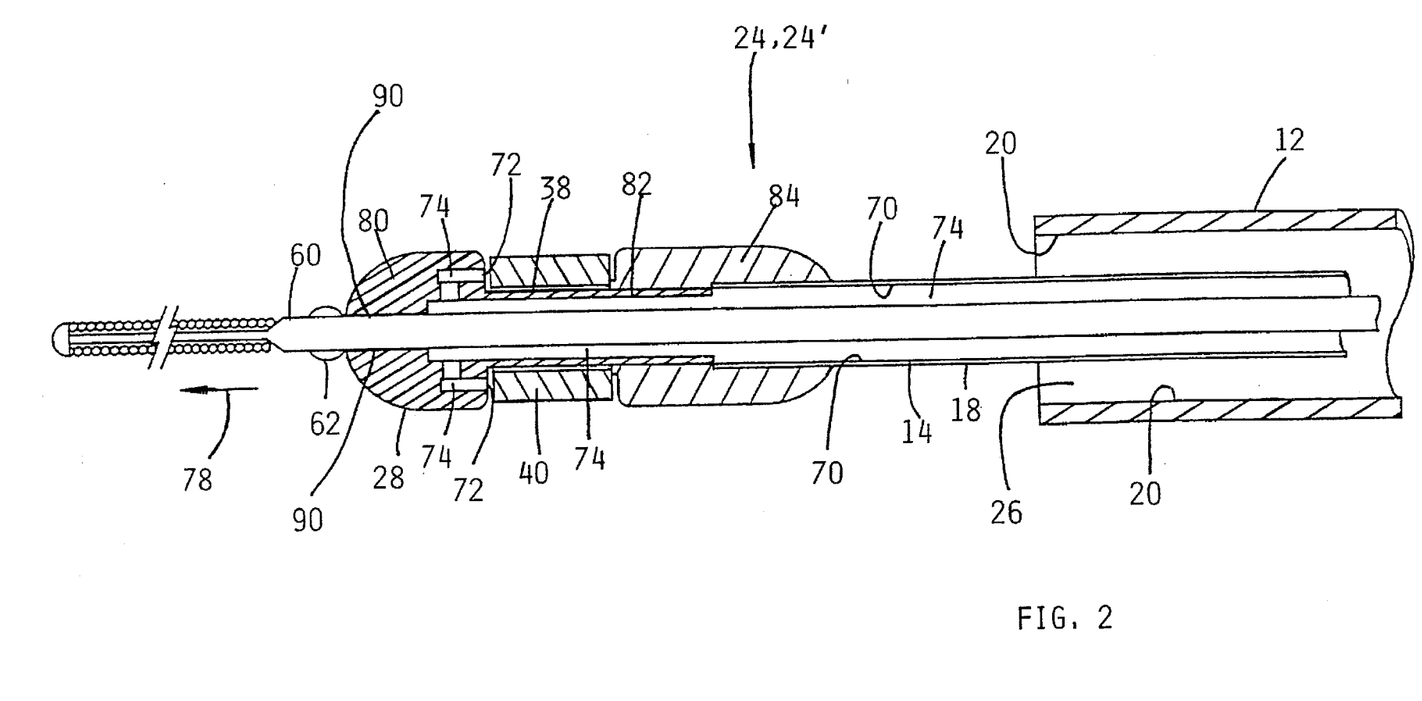
FIG. 2 is an enlarged, partial section view of working portion of a catheter of this invention.

FIG. 2 shows in section, the distal portion 24, 24' of catheter system shown in FIG. 1. In addition to showing the similarly numbered like features described in FIG. 1, there is shown the inner wall 70 of inner catheter body 14. Proximally directed orifices 72 in header 28 are shown to direct their exiting pressurized fluid against diffuser 40. Inner wall 70 in conjunction with header or manifold 28 defines central lumen 74 which is fluidically coupled through connector 30 to the proximal end of the catheter. Pressurized fluid introduced through connector 30 thus is delivered proximate or adjacent to the previously identified site of an occlusion.

Of particular note is the detailed interior structure of header or manifold 28. Header 28 comprises as head section 80 into which fluid is delivered and a throat section 82 which is an extension of lumen 74. Disposed about or around a portion of throat section 82 is a rounded sleeve 84 which serves to retain the entire header 28 adjacent the extreme distal end of inner catheter body 14. Sleeve 84 further serves to retain diffuser 40 about throat section 82 and permits it to rotate thereabout. In an alternative embodiment of this invention, diffuser 40 may be fixed to header 28 in which case it would not rotate when impinged by fluid exiting from orifice 72. Other than the need to receive fluid from central lumen 74 and to redirect it through orifices 72 the detailed design of header 28 is not particularly critical. Many other structures which permit utilization of a fixed or rotatable diffuser are possible in view of the present invention.

Also of note in FIG. 2 is the close tolerance fit between guidewire 60 and the reduced diameter section of central lumen 74 which is shown at interface 90. The close fit between guidewire 60 and central lumen 74 at interface 90 substantially prevents fluid from exiting distally from the catheter system. Pressurized fluid in inner lumen 74 therefore is delivered substantially proximally from orifice(s) 72 rather than distally i.e, in the direction of arrow 78. The close tolerance fit must be sufficiently close so as to prevent excessive proximal delivery of fluid (from central lumen 74) and yet permit the catheter system to pass over guidewire 60 to be positioned (and possibly repositioned) near an occlusion.

Exterior catheter body inner wall 20 and interior catheter exterior wall 18 define annular lumen 26. Annular lumen 26 is the structure into which dissolution products and fluid are aspirated through proximal manifold 50 to be removed from the occlusion site. Annular lumen 26 is fluidically coupled to an exterior aspiration (e.g., vacuum) source to draw fluid and debris therefrom.

Figure 3:
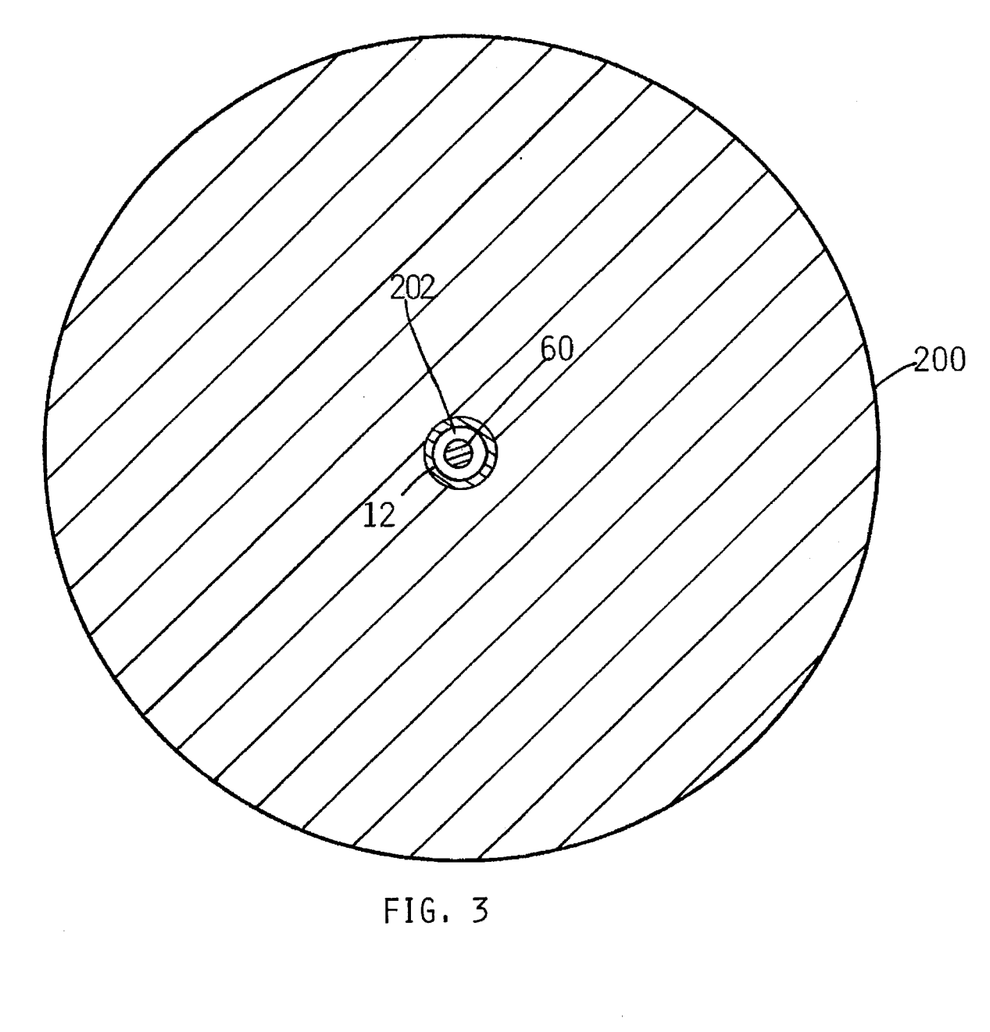
FIG. 3 is a cross-sectional view taken along line 3—3 of FIG. 1.

FIG. 3 is a cross-sectional, enlarged view taken along line 3—3 of FIG. 1. The cross hatched area of the catheter section is the substantially solid proximal coupler body 200. Through coupler body 200 is an axial lumen 202 which is or comprises a portion or extension of central lumen 74. Passing through lumen 202 is guidewire 60.

Figure 4:
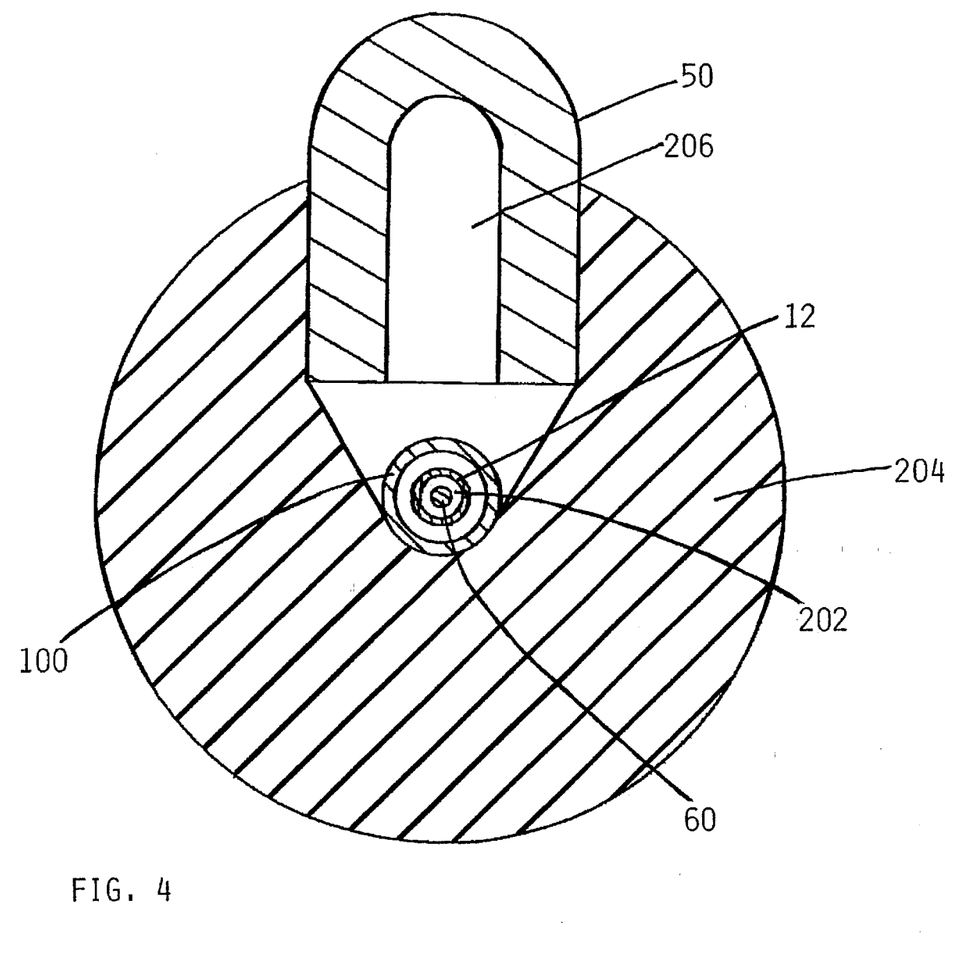
FIG. 4 is a sectional view taken along line 4—4 of FIG. 1.

FIG. 4 is an enlarged sectional view of the catheter system taken along line 4—4 of FIG. 1. FIG. 4 shows the internal details of the connection between luer coupler 50 and second coupler body 204. By means of angular orifice 206 a merger (and fluidic coupling) between luer coupler 50 and annular lumen 26 is completed. The particular arrangement used to effectuate fluidic coupling is not critical as long as the required functional attributes of the catheter system, i.e., steerability, aspiration, inspiration, and rotational fluid dispersion, are obtained.

Figure 5:
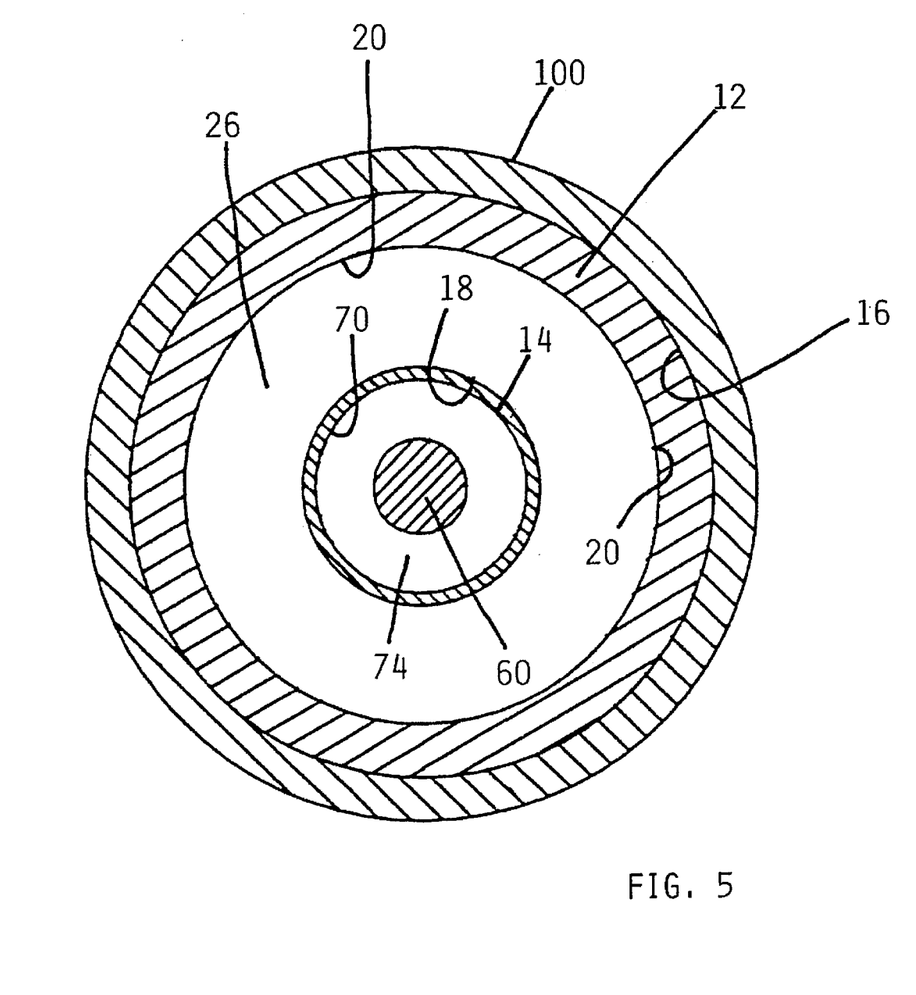
FIG. 5 is a cross-sectional view of the catheter of FIG. 1 taken along line 5—5 of FIG. 1.

FIG. 5 is a cross sectional view of a catheter of this invention taken along line 5—5 of FIG. 1. Shown in FIG. 5 are tubular support segment 100 from luer coupler 50, exterior catheter body wall 12 which has inner and outer sides 16, 20, inner catheter wall 14 which has inner and outer sides 18 and 70, annular lumen 26, central lumen 74 and guidewire 60. In this structure, luer coupler 50 slightly overlaps part of the proximal portion of outer catheter body wall 16 and is affixed thereto by means of, for example, an adhesive.

Figure 6:
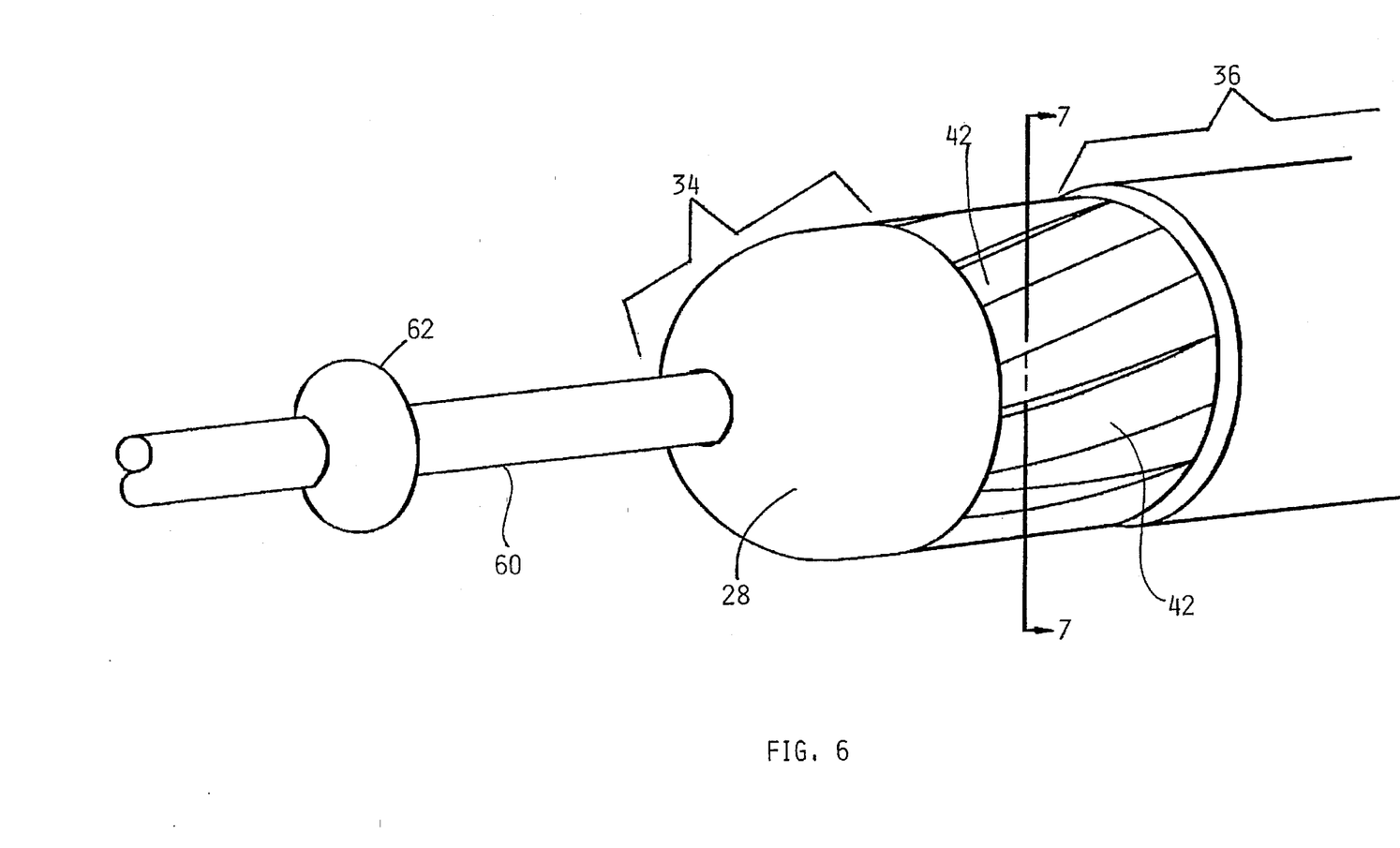
FIG. 6 is a detailed perspective view of a diffuser or rotor assembly of the present invention.

FIG. 6 is an enlarged, perspective view of the header/diffuser portion of a catheter system of this invention. Helical grooves 42 have been cut or formed into diffuser 40. The number, depth, orientation, and distribution of grooves (if grooves are employed) in the diffuser will determine the shape and dimension of the zone of dissolution. In the particular diffuser shown, helical grooves 42 are deeper toward the distal end of the system. The grooves become shallower and substantially merge with the surface or outer profile of the diffuser as they proceed toward the proximal end of the system and annular lumen 26. Essentially any groove configuration which directs fluid impinging thereon toward the obstruction to be treated is within the contemplation of the present invention. Generally speaking, such fluid will be radially directed and will rapidly rotate a rotatable diffuser.

Figure 7:
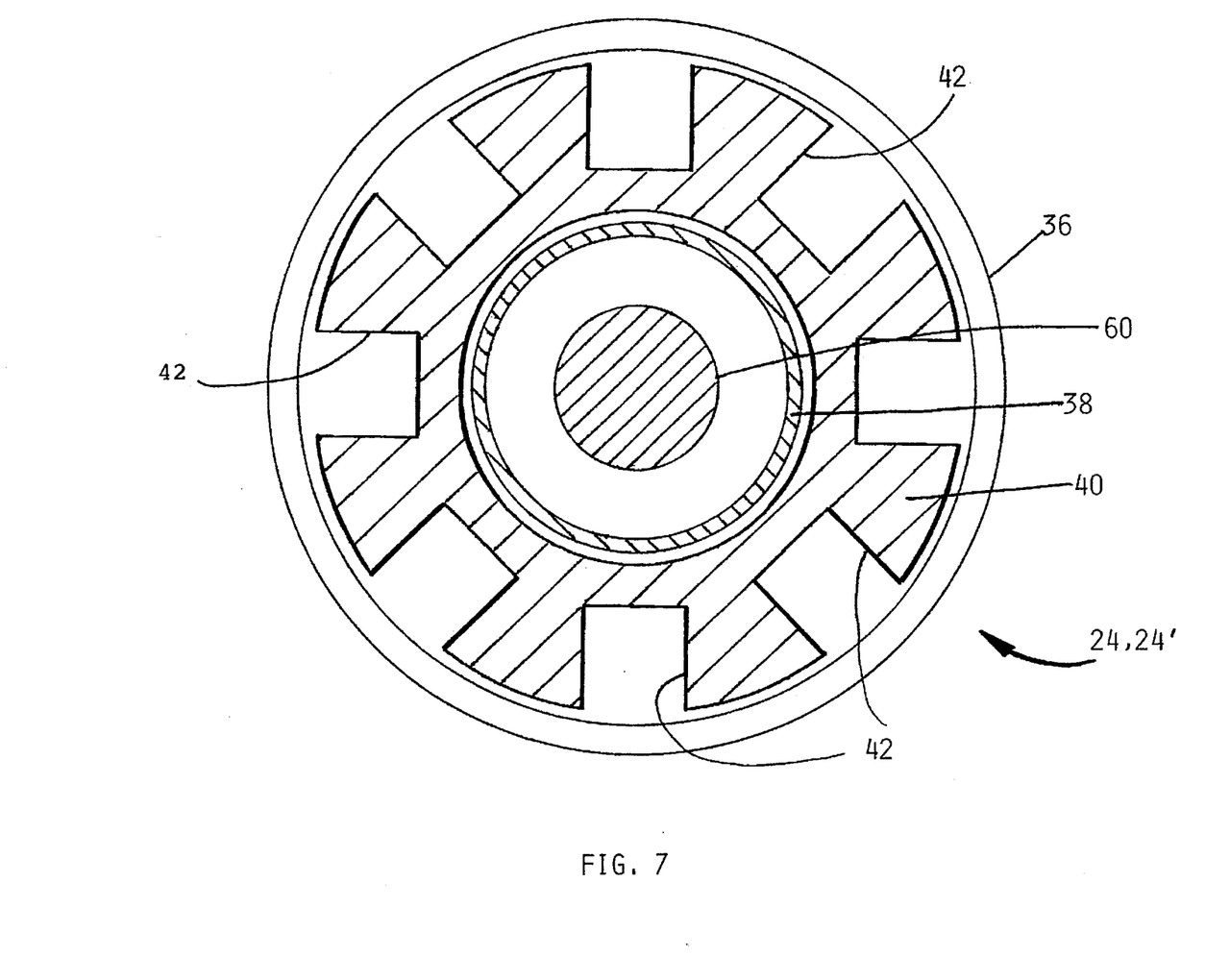
FIG. 7 is a cross-sectional view of the rotor assembly taken along line 7—7 of FIG. 6.

FIG. 7 is a sectional view of a catheter of this invention taken along line 7—7 of FIG. 6. Diffuser 40 with helical grooves 42 are shown in section. Also shown is the interaction between diffuser 40 and manifold medial segment 38. Medial segment 38 supports diffuser 40 and permits it to be rotated by impinging fluid. In this embodiment, manifold 28 includes all of the structure to deliver fluid proximally and disperse it radially. In variations on this structure, the diffuser could be supported by the inner catheter body and not be connected to or with the manifold structure. Other variations within the above teaching will occur to one skilled in this art in light of this disclosure.

As discussed above, in one embodiment this invention provides yet another significant advantage i.e., the ability to adjust the separation distance between the dissolution/diffuser segment from which fluid is delivered and the aspiration/annular lumen into which fluid and dissolution debris are withdrawn. This is accomplished by utilizing coupler bodies which are separate and are not coaxially fixed with respect to each other. Thus, for example, by separating luer couplers 30 and 50 with respect to each other (a interface 110) the separation between fluid delivery (at orifices 72) and fluid uptake (into annular lumen 26) can be adjusted. If a fixed relationship is intended, then a single luer connector block could be utilized with couplers 30 and 50 inputing to the same connector block structure, albeit to different lumens.

Figure 8:
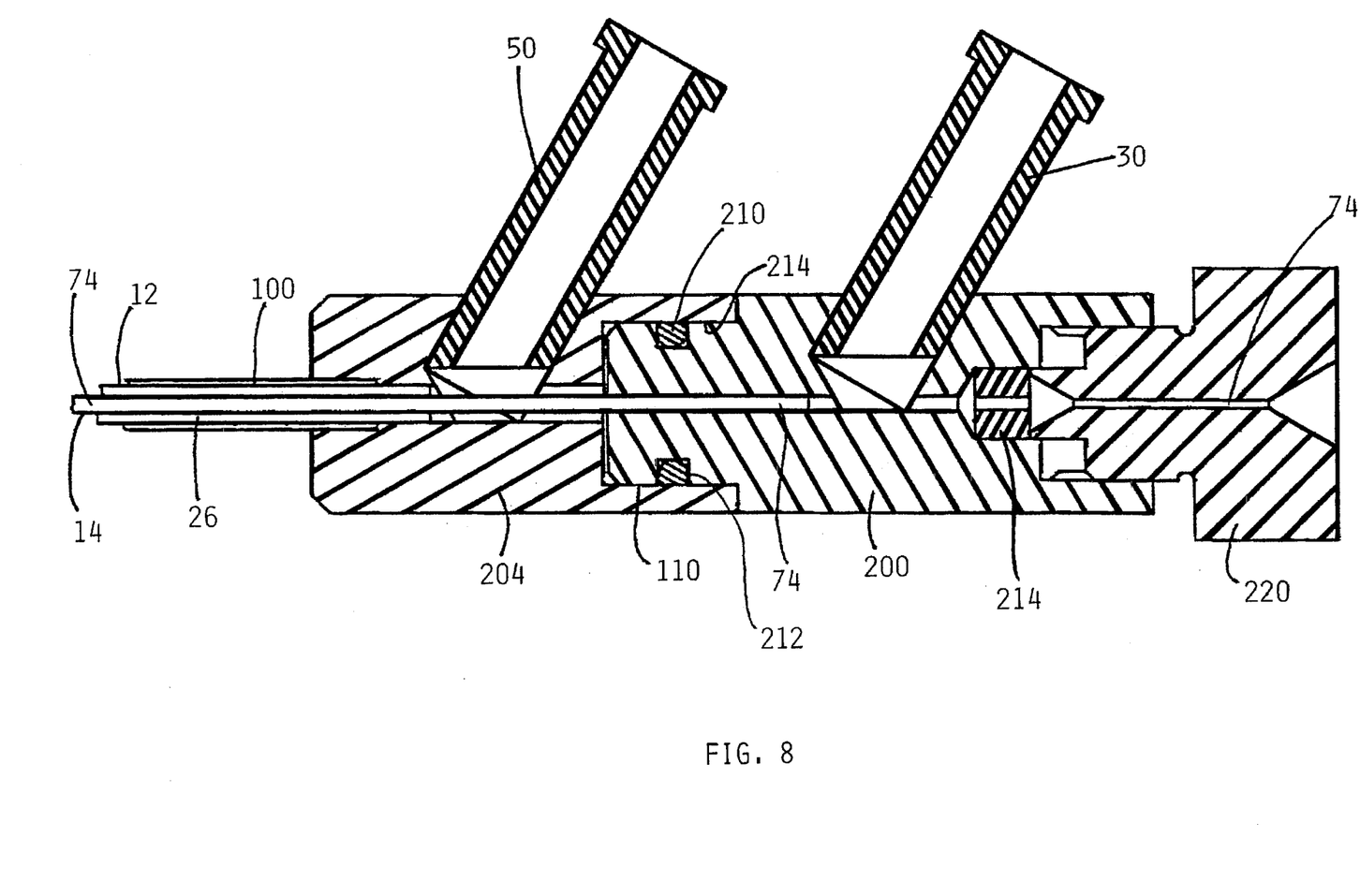
FIG. 8 is a sectional side view of the proximal portion of a catheter of FIG. 1.

FIG. 8 shows in section one connector block arrangement which is both substantially fluid tight and permits coupler bodies 200 and 204 to move axially with respect to each other. (No guidewire is shown in FIG. 8.) Proximal coupler body 200 is shown to couple into the proximal end of coupler body 204 (at interface 110) and by means of O ring 210. O ring 210 essentially prevents fluid from flowing through the coupler block interface which permitting the coupler blocks to be separated from each other. The coupler blocks are, in turn fixedly coupled to one or the other of the inner and outer catheter bodies such that separating the coupler block changes the extent of inner and outer catheter overlap. The compressed O ring is held in place by groove 212 and is compressed against the inside surface 214 to complete a fluid-tight connection.

Also shown in FIG. 8 is threaded connector 220. Threaded connector 220 cooperates with coupler body 200 to create a substantially fluid tight fit (when completely inserted) around a guidewire. Seal 214 creates this fluid-tight fit as threated connector 220 is threaded into coupler block 200. As shown, central lumen 74 runs completely through blocks 200,204 and 220. By virtue of the reduction in diameter through threaded connector 220 and manifold 28, the previously mutually exclusive goals of a steerable, rheolytic catheter system is obtained.

Figure 9:
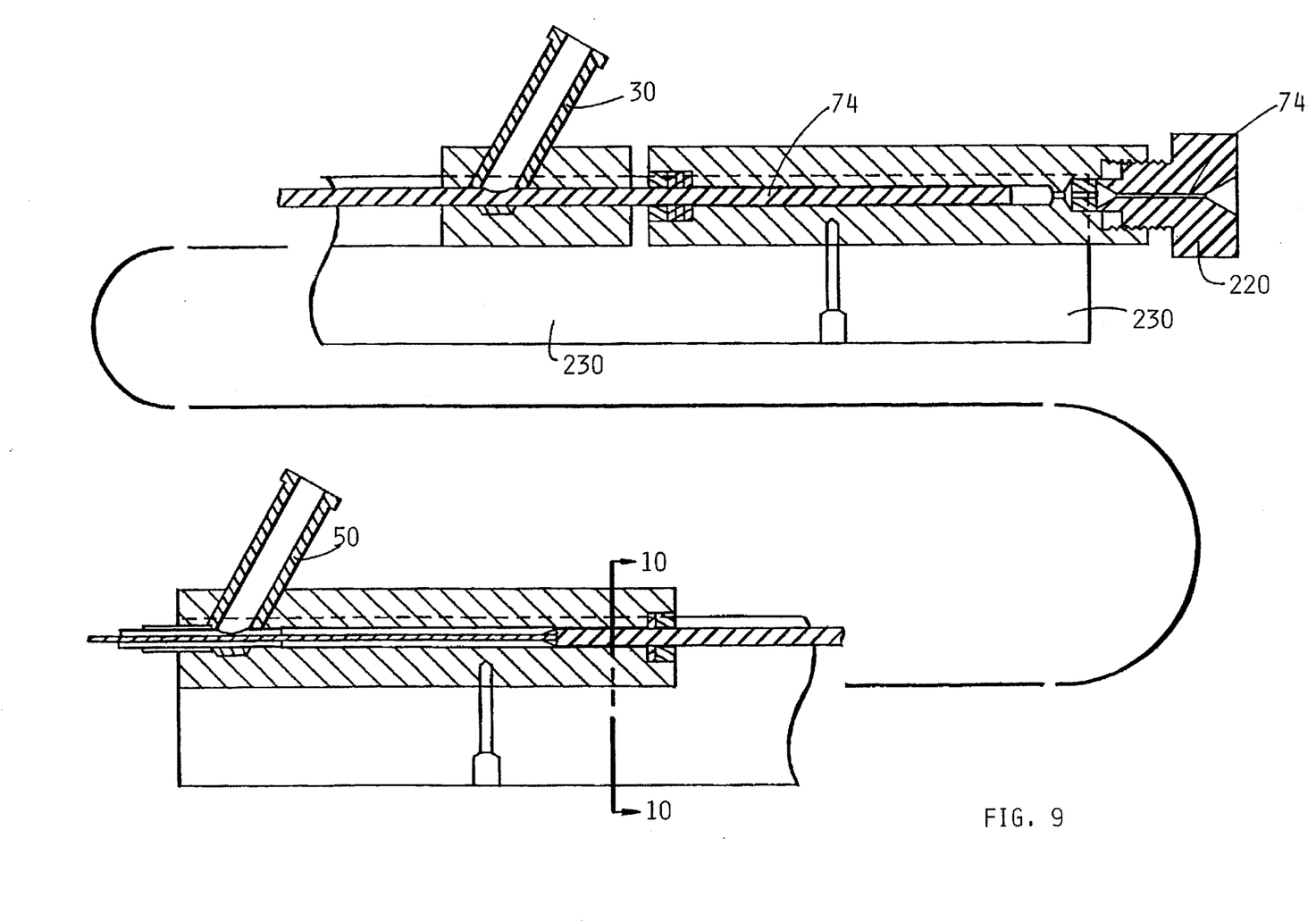
FIG. 9 is a cross-sectional view of a second embodiment of the present invention in which the inner and outer catheter body overlap is adjustable.
Figure 10:
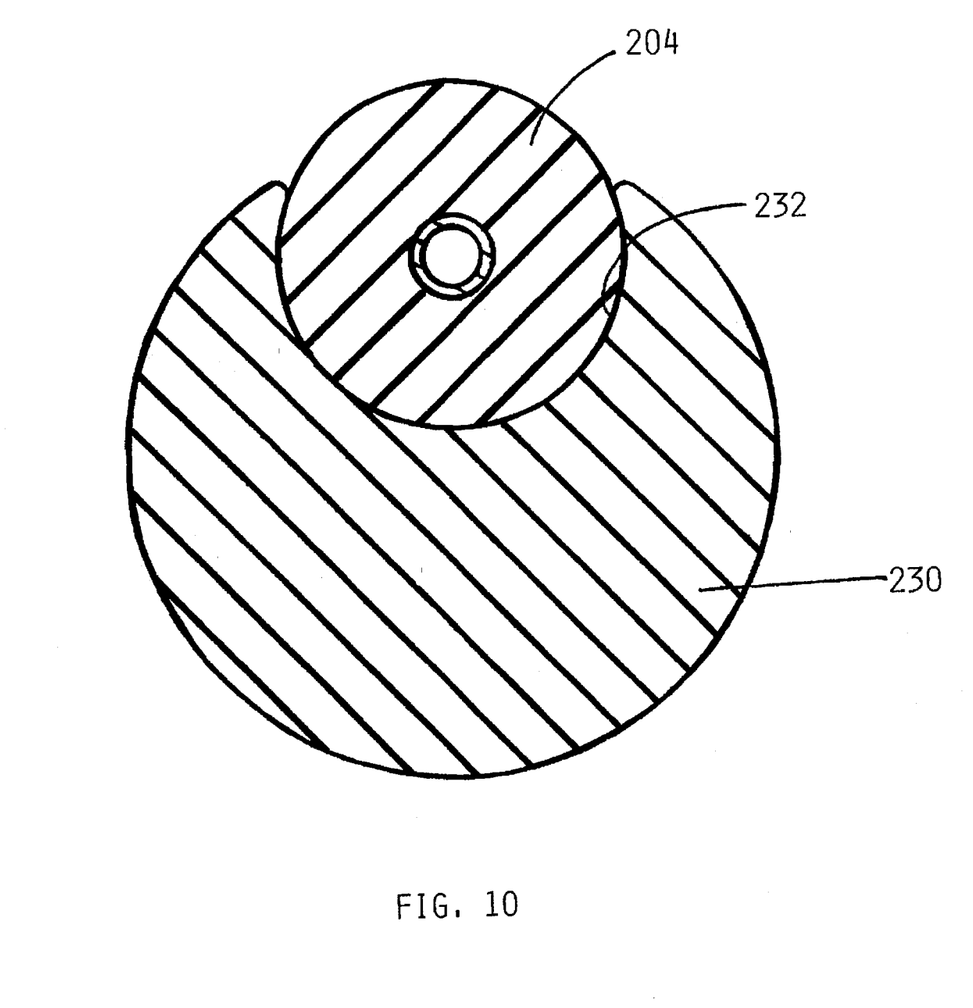
FIG. 10 is a cross-sectional view of the embodiment of the invention shown in line 10—10 of FIG. 9.

FIGS. 9 and 10 illustrate a variation upon the above-described system wherein coupler bodies 200 and 204 are supported and held in axial relation (so as to permit their axial movement) by a cylindrical support 230 having therein a cooperating arcuate groove 232. Cylindrical support 230 is substantially larger in diameter than eight of coupler bodies 200 or 204 and has groove 232 machined or formed along one side. The coupler bodies may then be slid into groove 232 to provide a proximal catheter configuration which is substantially integral and controllable with, for example, one hand. By virtue of this arrangement it becomes possible for the catheter to be held and controlled, for the axial length of the diffusion zone to be adjusted with coupler body 204 (an its associated assembly) being moved with respect to coupler body 200 (and its associated assembly).

FIG. 10 is a section view along line 10—10 of FIG. 9. FIG. 10 clearly shows the sliding relationship between coupler body 204 and cylindrical support 230. This sliding relationship suggest many alternative means in which diffusion zone linear dimension may be adjusted. For example, the handle means, discussed above could be attached to support 230 with trigger means coupled to the catheter segment which is to be moved. In this manner, convenient single-handed manipulation may be accomplished.

Figures 11, 12, 13, 14:
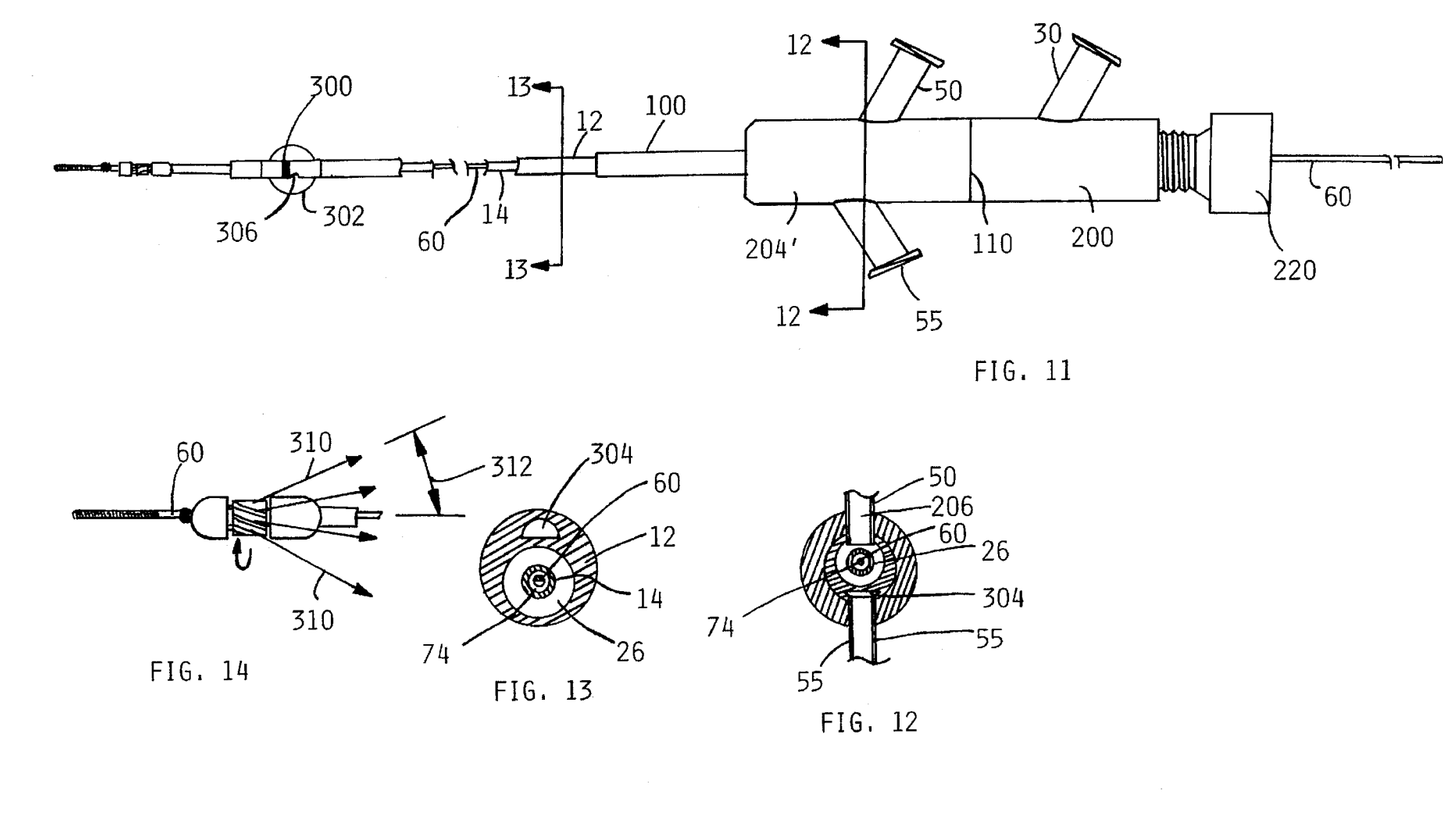
FIG. 11 is a plan view of another embodiment of a catheter of the present invention.
FIG. 12 is a sectional view of the catheter of FIG. 11 taken along line 12—12.
FIG. 13 is a sectional view of the catheter of FIG. 11 taken along line 13—13 of FIG. 11.
FIG. 14 illustrates flow of fluid from the catheter diffusion manifold.

FIGS. 11–13 illustrate yet another embodiment of the present invention in which a radiopacity marker band 300 and an inflatable balloon 302 are utilized on the catheter body. Balloon 302 is located on the outside wall 16 of outer catheter body 12. Such a balloon would be used to center the catheter system or to substantially restrict fluid flow down the vascular structure in which the catheter system is placed. Radiopacity marker bands or markers, which are visible under fluoroscopic examination, are utilized to locate the otherwise transparent balloon structure during catheter placement. Marker band 300, in this embodiment, is intended to indicate to the physician the location of balloon 302. Marker bands may be used elsewhere on (or within) the catheter to indicate to a user the location of significant structures in or on the catheter system.

FIGS. 12 and 13 are sectional views taken along line 12—12 and 13—13 of FIG. 11. FIGS. 12 and 13 illustrate a variation to distal coupler body 204' and to outer catheter body 12 necessary to accommodate the balloon structure. That variation is to provide a fluid connector 55 which is utilized to inflate and deflate balloon 302. Connector 55 is coupled to balloon 302 to permit fluid to be injected therein to inflate it. Through a third lumen 304 (best seen in FIG. 13) relatively incompressible fluid can be used to inflate and deflate balloon 302. Lumen 304 can be extruded into catheter body 12 in accordance with known techniques. Fluidic connection between connector 55 and balloon 302 is completed by means of skive 306 which intersects lumen 304.

FIG. 14 illustrates the flow of fluid from diffusion manifold 26 toward the proximal end of the catheter system. Fluid flow (and therefore the zone of turbulence or dissolution) is shown by arrows 310 and is produced by fluid exiting manifold 26 and impinging upon diffuser 40. Of particular note is the envelope or shape of the turbulence zone generated. Presuming that guidewire 60 lies approximately along the axis of the device, the fluid envelope, zone or cone may be defined by the interior angle between the catheter axis and the fluid around the catheter which is non-turbulent. Arrow 312 shows the approximate 40 degree interior angle subtended by the fluid emerging from the device (an impinging upon the diffuser) as would be generated in this embodiment. As noted above, it is control of this zone of destruction envelope which provides one of the many advantages of the present invention.

The above disclosure will suggest may alterations and variations to one of ordinary skill in this art. This disclosure is intended to be illustrative and not exhaustive. All such variations and permutations are to be included within the scope of the attached claims.

What is claimed is as follows:

1. A catheter system for removal of vascular obstructions comprising:
   a. inner and outer elongate, catheter bodies, each said bodies having catheter walls with inner and outer sides and distal and proximal ends, the distal end of the outer catheter body terminating short of the distal end of the inner catheter body;
   b. the inner catheter body wall defining a central lumen which fluidically couples the distal and proximal ends of the inner catheter, the central lumen being of a diameter which permits the lumen to receive and follow a guide means, and which cooperates with the guide means to prevent distal fluid delivery, the central lumen being fluidically coupled to:
   c. a diffusion manifold, the diffusion manifold being mounted on the distal end of the inner catheter and including a plurality of orifices, the system further including:
   d. diffuser means, said diffuser means being located between the distal end of said outer catheter and said diffusion manifold so that fluid exiting from the orifices impinges thereon, said inner and outer catheter walls defining:
   e. an annular lumen, the annular lumen extending from the distal end to the proximal end of the outer catheter body, the system also including;
   f. means to couple said central lumen to a source of pressurized fluid on its proximal end; and
   g. means to couple said annular lumen to aspiration means on its proximal end.

2. A system according to claim 1 wherein the inner and outer catheters are axially movable with respect to each other.

3. A system according to claim 1 wherein the inner and outer catheters are coupled by means of a cylindrical support which permits their coaxial relationship to be adjusted.

4. A system according to claim 1 wherein the diffuser means is rotatively mounted on a portion of said manifold.

5. A system according to claim 1 wherein the diffuser means comprises a portion of the exterior wall of the inner catheter body and is located proximal to said orifices.

6. A system according to claim 1 wherein the diffuser means comprises a rotatively mounted ring, said ring having a plurality of helical grooves in its external surface.

7. A system according to claim 1 wherein balloon means are mounted on the outer catheter, said balloon means including means to inflate and to deflate said balloon means.

8. A system according to claim 1 wherein radiopaque markers are located on said inner catheter.

9. A system according to claim 1 wherein said central lumen coupler means is a proximal luer connector.

10. A system according to claim 1 wherein said annular lumen coupler means is a proximal luer connector.

11. A catheter system for removal of vascular obstructions comprising:
   a. inner and outer elongate, catheter bodies, each said bodies having catheter walls with inner and outer sides and distal and proximal ends, the distal end of the outer catheter body terminating short of the distal end of the inner catheter body, the proximal ends of each said bodies being fluidically coupled to separate coupler bodies, said coupler bodies being axially aligned and wherein separation of said bodies changes the axial alignment of said catheter bodies;

b. the inner catheter body wall defining a central lumen which fluidically couples the distal and proximal ends of the inner catheter, the central lumen being of a diameter which permits the lumen to receive and follow a guide means, and which cooperates with the guide means to prevent distal fluid delivery, the central lumen being fluidically coupled to:

c. a diffusion manifold, the diffusion manifold being mounted on the distal end of the inner catheter and including a plurality of orifices, the system further including:

d. diffuser means, said diffuser means being located between the distal end of said outer catheter and said diffusion manifold so that fluid exiting from the orifices impinges thereon, said inner and outer catheter walls defining:

e. an annular lumen, the annular lumen extending from the distal end to the proximal end of the outer catheter body, the system also including;

f. means to couple said central lumen to a source of pressurized fluid on its proximal end through one of said coupler bodies; and g. means to couple said annular lumen to aspiration means on its proximal end through the other of said coupler bodies.

12. A system according to claim 11 which further includes a guidewire, said guidewire lying along the axis of the system and cooperating with said central lumen to restrict distal and proximal fluid flow from the system.

13. A system according to claim 11 which futher includes a threaded connector, said threaded connector having an axial, reduced diameter central lumen portion running therethrough, said threaded connector cooperating with the more proximal of said coupler blocks and being threaded therein to substantially restrict proximal fluid flow when a guidewire is located in said central lumen.

14. A method for removing an obstruction in a body vessel comprising the steps of:

identifying the site of the obstruction;
providing a catheter comprising:

a. inner and outer elongate, catheter bodies, each said bodies having catheter walls with inner and outer sides and distal and proximal ends, the distal end of the outer catheter body terminating short of the distal end of the inner catheter body;

b. the inner catheter body wall defining a central lumen which fluidically couples the distal and proximal ends of the inner catheter, the central lumen being of a diameter which permits the lumen to receive and follow a guide means, and which cooperates with the guide means to prevent distal fluid delivery, the distal end of the inner catheter being fluidically coupled to:

c. a diffusion manifold, the diffusion manifold including a plurality of fluid diffusion orifices, the system further including:

d. diffuser means, said diffuser means being located between the distal end of said outer catheter wall and said diffusion manifold so that fluid exiting from the orifices impinges thereon, said inner and outer catheter walls define:

e. an annular lumen, the annular lumen extending from the distal end to the proximal end of the outer catheter body, the system also including;

f. means to couple said central lumen to a source of pressurized fluid on its proximal end; and g. means to couple said annular lumen to aspiration means on its proximal end;

directing the diffusion manifold through the body vessel to a location adjacent the obstruction with a guide means;

coupling said central lumen to an external source of pressurized fluid;

coupling said annular lumen to an external aspiration means;

activating the external source of pressurized fluid and the external aspiration means so that said fluid flows from said manifold, impinges upon said diffuser and is directed toward said obstruction whereby said obstruction is impacted by said fluid and is at least partially removed, said destruction products of the obstruction being aspirated from the obstruction site through the annular lumen.

15. A method according to claim 14 wherein the fluid is delivered proximate the obstruction in a pulsatile fashion.

16. A method according to claim 14 wherein the directing step is accomplished by inserting a guide wire to a location near the obstruction, and sliding the catheter system over the guide wire until the distal end of the catheter is located proximate the obstruction.

17. A method according to claim 14 wherein said directing step is accomplished while monitoring radiopaque structures located on said system.

18. A method for removing an obstruction in a body vessel comprising the steps of:

generating a controllable zone of turbulence in the vicinity of the obstruction by means of a catheter by:

directing proximally a fluid at a diffuser means which atraumatically radially diffuses said fluid toward the obstruction until the obstruction is at least partially removed while recovering fluid and debris produced from the obstruction by the zone of turbulence.

19. A method according to claim 18 wherein fluid delivery, and fluid and debris recovery are accomplished simultaneously.

20. A method according to claim 18 wherein fluid delivery and fluid and debris recovery are accomplished sequentially.

21. A method according to claim 18 wherein the zone of turbulence is generated with a catheter comprising a rotating diffuser which directs a proximally directed fluid toward said obstruction, the obstruction being removed from the vessel without physical contact between the turbulence generating means and the obstruction.

22. A method according to claim 18 wherein fluid pressure, proximally directed orifice location, diffuser means external configuration and diffusion orifice, aspiration orifice separation are adjusted to create a zone of turbulence having an exterior envelope which falls in the interior angle range of about 5 to about 75 with respect to the axis of said catheter system.

* * * * *